United States Patent [19]

Littell et al.

[11] Patent Number: 5,114,720
[45] Date of Patent: May 19, 1992

[54] GELATIN COATED TABLETS AND METHOD FOR PRODUCING SAME

[75] Inventor: Charles A. Littell, Bellvale; Thomas W. Kucharski, Goshen; Michael K. Doelling, New York; Douglas C. Becker, Warwick, all of N.Y.

[73] Assignee: American Cyanamid Company, Stamford, Conn.

[21] Appl. No.: 634,902

[22] Filed: Dec. 27, 1990

[51] Int. Cl.$^5$ ............................................. A61K 9/40
[52] U.S. Cl. ................................ 424/478; 424/459; 424/460; 424/474; 424/475; 424/479; 424/492; 427/3
[58] Field of Search ............... 424/474, 478, 479, 460

[56] References Cited

U.S. PATENT DOCUMENTS 4,702,919 10/1987 Kitamori et al. ..................... 424/480
4,820,524 4/1989 Berta .................................... 424/463

FOREIGN PATENT DOCUMENTS 0835956 5/1960 United Kingdom ................ 424/478

Primary Examiner—Thurman K. Page
Assistant Examiner—James M. Spear
Attorney, Agent, or Firm—Thomas S. Szatkowski

[57] ABSTRACT

Pharmaceutical tablets having increased slipperiness and swallowability are provided. The enhanced swallowability is imparted by an overcoat of a low bloom gelatin, which overcoat has a lower coefficient of friction than other known coatings.

4 Claims, No Drawings

GELATIN COATED TABLETS AND METHOD FOR PRODUCING SAME

BACKGROUND OF THE INVENTION

1. FIELD OF THE INVENTION

The invention relates to tablets having a gelatin overcoat formed by spraying a low bloom gelatin and water solution onto a previously coated tablet, the gelatin coating imparting a low coefficient of friction and thus an increased slipperiness and swallowability to the tablet without the stickiness or thickness normally associated with gelatin type coatings. The invention also relates to a method of producing such tablets.

2. DESCRIPTION OF THE PRIOR ART

The pharmaceutical industry has long used empty gelatin capsules to encapsulate dosages forms of various medicines. Remington's Practice of Pharmacy, 17th Ed., p. 1625 to 1631. Recently, however, problems with tampering have caused a curtailment in consumer demand for capsule products. As a result, some producers have withdrawn their capsule products from the market and replaced them with pills, tablets or oblong shaped pills called caplets.

The coatings of pharmaceutical dosage forms such as pills or tablets utilizing rotating pan systems is well known. Typical coating processes include sugar coating which utilize coating powders such as sugar, acacia, flour, starch, are applied with an adhesive solution such as a viscous solution of acacia, gelatin or sugar and film coating which utilize film forming agents such as vinyl polymers, celluloses, acrylates, or natural gums and resins such as zein, gelatin, shellac and acacia. Remington, 17th Ed., p. 1623–1643.

In Japan patent No. 44-26677 to Daiichi Seiyaku Co. a method of manufacturing coated tablets is disclosed. Specifically the tablet is first undercoated with a first stage coating solution of 1 to 10 parts of a viscous substance such as gelatin, 30–70 parts of a solid filler such a titanium dioxide or talc and 48–60 parts of a solvent such as water. A heavy undercoat of approximately 170 mg is sprayed on in a coating pan apparatus followed by a second stage film coating of cellulose, vinyl resins of PEG. The method disclosed in the Japanese patent differs substantially from the novel coated tablet and method of the present invention because a solution of gelatin and solid filler is utilized as an undercoating. Such a solution, having a solid filler as a major component, would not impart a low coefficient of friction or slipperiness and swallowability to the tablets as would the solution of low bloom strength gelatin utilized in the present invention.

In U.S. Pat. No. 4,820,514, a method for coating a caplet with a gelatinous coating is described. The method so described involves dipping one end of the caplet and then the other end into a gelatinous solution to produce a coating having a thickness of about 5 to 40 mils (col 10 lines 56 to 60). The gelatin solution disclosed for use with this method includes a gelatin having a bloom strength from 150 to 270 bloom and may include other agents such as plasticzers, preservatives, color, opacifying agents, methylcellulose or polyvinyl alcohols. This patent also describes a failed attempt (col 2 lines 3 to 30) to coat caplets with gelatins using a coating pan system. The caplets so coated were said to have am insufficient coating thickness of only 6 mils and not to be as shiny as caplets coated by a dipping process. This patent thus teaches away from spray coating gelatin solution and would teach someone away from the coated tablet of the present invention having a low coefficient of friction and increased slipperiness and swallowability with less adhesion or tack. This patent also fails to recognize the beneficial effects of low bloom strength gelatin on the stickiness and thickness of the final product.

In Japanese 52-41213 to Freund Industrial Co., another coating application is disclosed. This patent discloses coating pills with a coating composition comprising low molecular weight gelatin, copolymer, titanium dioxide pigments, alcohol and water. Coating processes utilizing alcohol are not favored due to environmental restrictions. The tablets of the present invention do not utilize alcohol.

In U.S. Pat. No. 3,962,384 a spray drying or agglomorating system is described, in which emulsions of gelatin and vitamin E are sprayed. This patent discloses O bloom strength gelatins as the preferred gelatins. However, there is no teaching of using such gelatins for coatings. Nor is there any teaching or suggestion of the decreased coefficient of friction, increased slipperiness and swallowability imparted to previously film coated tablets by such gelatin. The gelatin is used in the situation described in this patent as a binder. Use of gelatin as a binder would not suggest that an overcoat of a low bloom gelatin would have decreased coefficient of friction.

In U.S. Pat. No. 4,702,919 a fluidized bed granulation method which includes spraying a binder solution which comprises 1–10% binder is described. Col 2 line 41 identifies gelatin as one of sixteen (16) suitable binders. Suitable solvents include water as well as organic solvents. At col. 2 line 60 it is described that a viscosity of 1 to 1000 cp, with 10 to 500 being preferred, is necessary for spraying.

In U.S. Pat. No. 4,816,259 types of gelatins suitable for producing soft gelatin capsules are described as 130-200 bloom alkali skin or bone type (col 2 line 26).

In U.S. Pat. No. 3,141,792 pan coating apparatus and standard compositions components are described. Coating-pan systems such as the "Vector-Freund Hi-Coaters", sold by Vector Corporation, 675 44th Street, Marion, Ia. or the "GC-1000, GC-1250 or GC-1750" sold by Glatt Air Techniques, 20 Spear Road, Ramsey, N.J. are well known. These coating pan systems include a rotating drum to hold the pills or tablets to be coated and an air-atomization and spray gun inserted into the center of the drum for spraying a mist of the coating material on the caplets, capsules or tablets.

SUMMARY OF INVENTION

It has now been found that an improved coated pill or tablet having a low coefficient of friction, increased slipperiness and swallowability without stickiness or tackiness is produced by applying a thin overcoat of a low bloom strength gelatin solution over a previously coated pill. The low bloom strength gelatin overcoat according to the present invention is present in an amounts effective to impart a low coefficient of friction, improve slipperiness without tack, such effective amount preferably from 1 to 4 mils thickness or 3 to 5 mg weight. In addition, it has been found that a solution consisting essentially of gelatin of 0 to 80 bloom strength gelatin, water and flavor provide the required slipperiness without tack. The solution is sprayed onto the previously coated tablets utilizing known coating pan systems.

DESCRIPTION OF THE PREFERRED EMBODIMENTS

The tablets which may be coated according to the present invention include all types of pills, tablets and caplets for which coatings are desired. Typical tablets include multi -- vitamin compositions, antihistamines and analgesics. Tablets of various shapes and sizes such as round, oval and capsule may be employed.

Preferred are tablets which have been precoated with a undercoat of hydroxypropyl methyl cellulose, methyl cellulose, certain copolymers of methacrylic acid, and methylmethacrylate combined with a suitable plasticizer, opacifier and pigment to 2% -3% by weight of the total tablet weight. Typical plasticizers include glycerin, propylene glycol, polyethylene glycols, triacetin, acetylated monoglycerides, citrate esters, phthalate esters, and mineral oil. Typical opacifiers include titanium dioxide. Typical pigments include lake or water soluble dyes.

Gelatin coating compositions according to the present invention consist essentially from about 0.5 to 20 wt% of 0-80 bloom strength gelatin, and about 80 to 99.5 wt% water. Gelatins which may be utilized include calf skin, pork or bone.

The unexpected benefits of the overcoating with low bloom gelatin are described in greater detail with reference to the following examples.

Three (3) types of coatings were compared: low bloom gelatin overcoat according to the present invention, standard film coat and dipped high bloom gelatin. All tablet cores coated are ⅜" diameter flat faced bevel of 1.400 g tablet weight. The coating apparatus is a Glatt GC-300 pan coater and the equipment operating parameters are consistent for this apparatus. It will be appreciated that other types and sizes of film coating equipment will require adjustment to the equipment operating parameters so as to be consistent with the particular apparatus utilized to produce the requisite weight and thickness of gelatin coating.

EXAMPLE 1

| 1. Gelatin Solution for Spray Coating Formula: | |
|---|---|
| Gelatin - 0 Bloom | 70 g |
| Purified Water, USP | 930 g |
| TOTAL | 1000 g |

Process
A. Add gelatin - zero bloom to the purified water slowly with agitation at room temperature.
B. Mix for 15 minutes or until dissolved.
Application
A. Into a Glatt GC-300 pan coater, place 3.0kg of tablets previously undercoated with HPMC at a level of 35 mg per tablet (individual wt. =1,4g).
B. Begin tumbling the tablets at 10 rpm with an inlet temperature of 70° C. and inlet air volume of 120M³/hr.
C. When the outlet temperature reaches 40° C., begin spraying the gelatin solution at 12b/min. at 1.25 bar atomization air pressure. A total of 129g gelatin solution is applied to obtain a gelatin overcoat of 4mg/tablet having a thickness of 1 to 4 mils.

D. Maintain the outlet air temperature between 40°-45° C. for duration of the spray period.
E. When the appropriate amount of solution has been applied, continue drying the tablets at the above stated inlet condition for an additional 2 minutes.
F. Remove the gelatin overcoated tablets from the GC-300.

EXAMPLE II

| 1. Standard Film Coating Solution for Spray Coating Formula: | |
|---|---|
| Opradry Gray (4S-1-7568)* | 107 g |
| Purified Water, USP - | 617 g |
| TOTAL | 724 g |

*Opadry is a trademark of Colorcon, Inc., of West Point, Pennsylvania. They are a major supplier of premixed film coats to the pharmaceutical industry. Their formula consists of hydroxypropylmethyl cellulose (HPMC) used as a film former polysorbate 80 as a preservative, titanium dioxide as a opacifier, and an aluminum lake dye system to provide a desired color, in this case, gray.

Process
A. Add the opadry gray to the purified water slowly with agitation at room temperature.
B. Mix for 15 minutes or until dissolved.
Application
A. Into a Glatt GC-300, place 3.0 kg of tablets to be coated (individual wt =1.4g).
B. Begin tumbling the tablets at 10 rpm with an inlet air temperature of 70° C. and inlet air volume of 120 m³/hr.
C. When the outlet temperature reaches 40° C., begin spraying the film coat solution at 12g/min. at 1.25 bar atomization air pressure. A total of 510g of film coating solution must be applied to obtain 35 mg/tablet.
D. Maintain the outlet temperature between 40°-45° C. for duration of the spray period.
E. When the appropriate amount of solution has been applied, continue drying the tablets at the above stated inlet condition for an additional 2 minutes.
F. Remove the film-coated tablets from the GC-300.

EXAMPLE 3

| 1. Gelatin Solution for Tablet "Dipping" Formula: | |
|---|---|
| Bone gelatin - 150 bloom | 537 g |
| Glycerin USP | 201 g |
| Purified Water | 315 g |
| TOTAL | 1053 g |

Process
A. Mix glycerin and water together and heat to 80° C.
B. Add the glycerin/water mixture to the gelatin with agitation and heat to 80° C.
C. Deaerate to remove bubbles.
Application
A. Manually dip each tablet into the gelatin solution until full coverage.
B. Suspend coated tablet above gelatin until smooth coating results.
C. Air-tumble tablets for about 30 minutes.
D. Air dry coated tablets on trays for 24 hours.

DETERMINATION OF COEFFICIENT OF FRICTION

The coefficient of friction is determined by observing individual tablets on a ramp. Each tablet is tested on different slopes; the tangent of the angle at which the tablet moves at constant speed is the coefficient of friction (i):

Method

Ten (10) tablets of each coating were examined individually in the following way. The tablet was placed on a metal plate flat-face down and observed on different slopes. When constant velocity was observed, the height of the upper end of the plate was measured (O), as well as the horizontal distance from each end of the plate (A), and recorded.

Calculation

Dividing the height (O) by the horizontal distance (A) results in the coefficient of friction as reported by Giancoli, Douglas C. (1980). Physics. Prentice-Hall, Englewood Cliffs, N.J. Pages 49–51.

RESULTS OF COEFFICIENT OF FRICTION TESTING

| RESULTS OF COEFFICIENT OF FRICTION TESTING Example #1 Low Bloom Gelatin Over Coated Tablets | | | |
|---|---|---|---|
| Tablet | O (cm) | A (cm) | u |
| 1 | 7.0 | 27.1 | 0.258 |
| 2 | 6.9 | 26.7 | 0.258 |
| 3 | 6.9 | 26.9 | 0.257 |
| 4 | 7.0 | 26.5 | 0.264 |
| 5 | 7.2 | 26.4 | 0.273 |
| 6 | 6.9 | 26.9 | 0.257 |
| 7 | 6.2 | 26.7 | 0.232 |
| 8 | 7.2 | 26.4 | 0.273 |
| 9 | 7.2 | 26.4 | 0.273 |
| 10 | 6.9 | 26.6 | 0.259 |
| | | | $x_{10}$-0.260 |

| Example #2 Standard Film Coat | | | |
|---|---|---|---|
| Tablet | O (cm) | A (cm) | u |
| 1 | 7.6 | 26.7 | 0.285 |
| 2 | 8.0 | 26.7 | 0.300 |
| 3 | 7.9 | 26.5 | 0.298 |
| 4 | 7.7 | 26.5 | 0.291 |
| 5 | 7.4 | 26.7 | 0.277 |
| 6 | 7.5 | 26.8 | 0.280 |
| 7 | 6.2 | 26.7 | 0.281 |
| 8 | 8.0 | 27.0 | 0.296 |
| 9 | 7.9 | 26.9 | 0.294 |
| 10 | 8.3 | 27.0 | 0.307 |
| | | | $x_{10}$-0.291 |

| Example #3 Gel-Dipped Tablets | | | |
|---|---|---|---|
| Tablet | O (cm) | A (cm) | u |
| 1 | 7.6 | 26.7 | 0.270 |
| 2 | 9.3 | 25.7 | 0.362 |
| 3 | 7.3 | 26.9 | 0.271 |
| 4 | 7.3 | 26.9 | 0.271 |
| 5 | 7.9 | 26.5 | 0.298 |
| 6 | 7.7 | 26.8 | 0.287 |
| 7 | 7.2 | 26.7 | 0.270 |
| 8 | 7.7 | 26.8 | 0.287 |
| 9 | 8.3 | 26.7 | 0.311 |
| 10 | 7.7 | 26.8 | 0.287 |
| | | | $x_{10}$-0.291 |

As can be seen from the above results the coefficients of friction between gel "dipped" tablets and the standard film coat result in the same mean value. However, there seems to be more variability with the gel "dipped" tablets.

The low bloom gelatin over coated tablets according to the present invention demonstrate a mean coefficient of friction of 11% less than the gel "dipped" tablets or the standard film coat. This is a significant reduction in coefficient of friction and results in a tablet having easier swallowability than the tablets having the other coatings tested.

We claim:

1. A coated tablet which consists essentially of a tablet core coated with an undercoating comprising about 2 to about 3 wt% of the total tablet weight and a gelatin overcoat having a thickness of from about 1 to 4 mils, said overcoat formed by spraying a composition consisting essentially of:
0.5 to 20 wt% gelatin having a bloom strength of 0 to 80, and
80 to 99.5 wt% water.

2. A method for overcoating a coated tablet which consists essentially of spraying a sufficient amount of a coating composition consisting essentially of:
0.5 to 20 wt% gelatin having a bloom strength of 0 to 80, and
80 to 99.5 wt% water
onto a previously coated tablet in a rotating pan apparatus such that a gelatin overcoat having a thickness of from 1 to 4 mils is imparted to said tablet.

3. The tablet according to claim 1 wherein said gelatin has a bloom strength of about 0.

4. The method according to claim 2 wherein said gelatin has a bloom strength of about 0.

* * * * *